United States Patent
Kamahori et al.

(10) Patent No.: US 8,383,396 B2
(45) Date of Patent: *Feb. 26, 2013

(54) APPARATUS AND METHOD FOR MEASURING BIOLOGICAL MATERIAL

(75) Inventors: Masao Kamahori, Kokubunji (JP);
Yoshiaki Yazawa, Nishitokyo (JP);
Maki Shimoda, Hino (JP)

(73) Assignee: Hitachi, Ltd., Tokyo (JP)

( * ) Notice: Subject to any disclaimer, the term of this patent is extended or adjusted under 35 U.S.C. 154(b) by 897 days.

This patent is subject to a terminal disclaimer.

(21) Appl. No.: 11/072,507

(22) Filed: Mar. 7, 2005

(65) Prior Publication Data

US 2006/0016699 A1    Jan. 26, 2006

(30) Foreign Application Priority Data

Jul. 21, 2004   (JP) ................................ 2004-213130

(51) Int. Cl.
*C12M 1/34* (2006.01)
*C12M 3/00* (2006.01)

(52) U.S. Cl. ................... 435/287.2; 435/6.1; 435/285.2; 422/68.1; 422/82.01

(58) Field of Classification Search .... 422/82.01–82.03, 422/68.1, 131, 186; 435/6.1, 7.1, 91.1, 283.1, 435/285.2, 287.2, 287.3, 287.4, DIG. 49; 427/2.13; 436/149, 501, 518, 525; 324/658–690
See application file for complete search history.

(56) References Cited

U.S. PATENT DOCUMENTS 4,020,830 A * 5/1977 Johnson et al. ................ 600/348
4,437,969 A * 3/1984 Covington et al. ............ 257/253
4,490,216 A * 12/1984 McConnell ................ 205/777.5
4,778,769 A 10/1988 Forrest et al.
5,164,319 A * 11/1992 Hafeman et al. ........... 435/287.1

(Continued)

FOREIGN PATENT DOCUMENTS

EP          631130 A2     12/1994
WO      WO 97/39145       10/1997

OTHER PUBLICATIONS

Nirmalya K. Chaki, K. Vijayamohanan, "Sefl-assembled monolayers as a tunable platform for bioensor applications", Biosensors & Bioelectronics, vol. 17, Jan. 2002 (available online Dec. 6, 2001), pp. 1-5 & 7.*

(Continued)

*Primary Examiner* — Michael Hobbs
(74) *Attorney, Agent, or Firm* — Stites & Harbison, PLLC; Juan Carlos A. Marquez, Esq; Stephen J. Weyer, Esq.

(57) ABSTRACT

Disclosed is a biomolecular detection device that can be used easily, at a low operating cost, and with a detection probe that can be immobilized easily. Using an insulated gate field effect transistor having a conductive electrode on the gate insulator between a source and a drain, a probe for detecting biomolecules is immobilized on the surface of the conductive electrode. For analysis, a conductive electrode on which a probe for detecting biomolecules is immobilized on the surface, and a reference electrode are placed in the sample solution in the analytical cell, an alternating current voltage is applied from a power source to the reference electrode and the electrical characteristics of the insulated gate field effect transistor that changes before and after binding of the measurement target substance such as DNA and proteins included in the sample solution with a probe for detecting biomolecules, namely the changes in the current values running between the source and the drain, are detected.

30 Claims, 16 Drawing Sheets

U.S. PATENT DOCUMENTS

| | | | |
|---|---|---|---|
| 6,355,436 | B1 | 3/2002 | Martin et al. |
| 6,413,792 | B1 * | 7/2002 | Sauer et al. ............ 438/49 |
| 6,653,687 | B1 * | 11/2003 | Yamazaki ............ 257/345 |
| 8,202,409 | B2 * | 6/2012 | Ishige et al. ............ 204/403.14 |
| 2002/0137083 | A1 * | 9/2002 | Kobori et al. ............ 435/6 |
| 2002/0179439 | A1 * | 12/2002 | Weng et al. ............ 204/400 |
| 2003/0073071 | A1 * | 4/2003 | Fritz et al. ............ 435/4 |
| 2003/0170698 | A1 * | 9/2003 | Gascoyne et al. ............ 435/6 |
| 2004/0126814 | A1 * | 7/2004 | Singh et al. ............ 435/7.1 |
| 2004/0175747 | A1 * | 9/2004 | Han et al. ............ 435/6 |
| 2005/0164286 | A1 * | 7/2005 | O'uchi et al. ............ 435/6 |
| 2006/0141474 | A1 * | 6/2006 | Miyahara et al. ............ 435/6 |

OTHER PUBLICATIONS

Thomas Kodadek. "Development of protein-detecting microarrays and related devices", Trends in Biochemcial Sciences, vol. 27, No. 6 Jun. 2002 pp. 295-300.*

Souteyrand et al. "Direct Detection of the Hybridization of Synthetic Homo-Oligomer DNA Sequences by Field Effect" J. Phys. Chem. B. 1997, 101, 2908-2985. Mar. 15, 1997.*

European Search Report dated Dec. 2, 2005.

Hashimoto, K., et al, "Sequence-Specific Gene Detection with a Gold Electrode Modified with DNA Probes and an Electrochemically Active Dye", Analytical Chemistry, vol. 66, No. 21, Nov. 1, 1994, pp. 3830-3833.

* cited by examiner 132  133

131

APPARATUS AND METHOD FOR MEASURING BIOLOGICAL MATERIAL

CLAIM OF PRIORITY

The present application claims priority from Japanese application JP 2004-213130 filed on Jul. 21, 2004, the content of which is hereby incorporated by reference into this application.

FIELD OF THE INVENTION

This invention relates to a detection device and a method for measuring biological materials, particularly DNA and proteins in a non-modified form. In particular, it relates to a detection device and a detection method using particularly a field effect transistor.

BACKGROUND OF THE INVENTION

With the recent progress in base sequence analysis technology, all base sequences of the human genomes have been analyzed and diverse utilization of DNA base sequence information in the medical field has been developed actively. Now it is expected that individual body types will be analyzed as well as diseases diagnosed at the individual level by understanding the status of gene expression in the biological systems in an attempt to contribute to individualized medical care suited for individual body types. We expect a dramatic development in broad fields including genetic engineering for agricultural products besides the development in medicine. The basis of such development is information on gene expression and functional information as well as information on base sequences. Currently functions of genes are investigated in a large scale using DNA chips and the expressions are being analyzed. Since a fluorescent detection method is the basic principle when using DNA chips and laser beams and complicated optical systems are required, the measurement systems are large and cost more. In order to circumvent the above problems, current detection type DNA chips using redox labeled materials or DNA sensors by detecting surface potentials using electrical characteristics of transistors have been reported. For the DNA chips using electrical measurements, it is easier to develop smaller equipment and the manufacturing cost can be reduced easily. Therefore, DNA chips using electrical measurements are currently attracting tremendous attention as a method suited for large capacity.

A current detection method using redox labeled materials is based on the properties that redox materials undergo intercalation among the double stranded DNA formed by binding of a target DNA to a DNA probe (called hybridization). The presence/absence of bindings between the target DNA and the DNA probe (hybridization) is determined by detecting the reception of electrons between the intercalated redox materials and the metal electrodes (Analytical Chemistry 66, (1994) 3830-3833).

According to the surface potential detection method using the electrical characteristics of transistors, a DNA probe is immobilized on the gate insulating layer on the source electrode and drain electrode, and the surface potential on the insulating film (surface charge density) when the target DNA binds to the DNA probe (hybridization) is then detected as changes in the current values between the source electrode and the drain electrode (Published Japanese translation of PCT international publication for patent application No. 511245/2001). As a gate insulator, materials such as silicon oxide, silicon nitride, and tantalum oxide are combined or used alone. In order to maintain good operation of transistors, a double structure is prepared by laminating silicone nitride or tantalum oxide on silicon oxide. In order to immobilize the DNA probe on the gate insulating layer, the gate insulating material surface is chemically modified using aminopropyl silane or polylysine to introduce amino groups and the DNA probe that has been chemically modified by the terminal amino groups is reacted using glutaraldehyde and phenylenediisocyanate.

[Non-patent Document 1] Analytical Chemistry 66, (1994) 3830-3833

[Patent Document 1] Published Japanese translation of PCT international publication for patent application No. 511245/2001

SUMMARY OF THE INVENTION

The basic principle of the current detection system using redox labeled substances is to detect oxidation and reduction current on a metallic electrode. If an oxidative substance or a reductive substance is present in the test sample, a current flows due to the coexisting substances, which interferes with detection of genes. In addition, electrochemical reactions proceed on the metallic electrode surface along with measurement of the current, which causes corrosion of the electrode and generation of gases. The problem is that the measurement conditions become unstable so that the detection sensitivity and detection accuracy are impaired.

In contrast, a surface potential detection method using electrical characteristics of transistors has no problem with corrosion of the insulating layer on the chips, generation of gases and interference with coexisting oxidative and reductive substances compared to the current detection system. However, in the structure employed by this method, an insulating layer also acts as a sensing unit and sizes and positions of the sensing unit greatly depend upon the structure of the transistor. In addition, it is necessary to prepare individual sensor chips in different shapes (transistors) based on the target substances of measurement. Immobilization of a DNA probe on a gate insulating layer requires complex pre-treatments such as silane coupling.

The purpose of the present invention is to provide a biomolecular detection device, particularly a DNA chip that can be used easily, at a low operating cost with the advantage that the detection probe can be immobilized easily.

To achieve the aforementioned purpose, a conductive electrode for immobilization of a detection probe and an insulated gate field effect transistor gate are connected with a conductive wire in a biomolecular detection device of this invention. The advantage when employing this structure is that an electrode for probe immobilization can be formed at an arbitrary place in an arbitrary size. It is also easy to increase electrode area for probe immobilization to improve measurement sensitivity. Moreover, when preparing different sensor chips for different subjects of measurements, there is no need to prepare them individually. The parts other than the electrodes for probe immobilization can be prepared using conventional semiconductor processes, and at last step a subject of measurement can be immobilized to an electrode for probe immobilization, which can significantly reduce manufacturing costs.

The effect of an electric double layer on the electrodes that is of concern when using a conductive electrode in a solution can be easily eliminated by applying an alternating voltage between a conductive electrode and a reference electrode. In this case, connection between the detection probe and the subject of measurement is not broken when applying this alternating voltage. If a noble metal such as gold is used as a conductive electrode, no reactions occur on the electrode surface in the solution. When using gold as a conductive electrode, a detection probe having an alkane thiol at the end can be immobilized by a simple operation such as dropping or spotting a detection probe solution on the gold electrode surface.

According to this invention using an insulated gate field effect transistor in which a detection probe has been immobilized on the conductive electrode surface as a biomolecular detection device, the presence/absence of a subject of measurement such as DNA and proteins included in the sample solution can be detected by detecting the changes in the electrical characteristics of the insulated gate field effect transistor that occur before and after binding between the subject of measurement including DNA and proteins in the sample solution and the biomolecular detection probe. The effect of an electric double layer on the electrode surface that is of concern can be easily eliminated by applying an alternating voltage between the electrode and the reference electrode.

DETAILED DESCRIPTION OF THE PREFERRED EMBODIMENTS

Embodiments of this invention will be described below with reference to the drawings.

Figure 1:
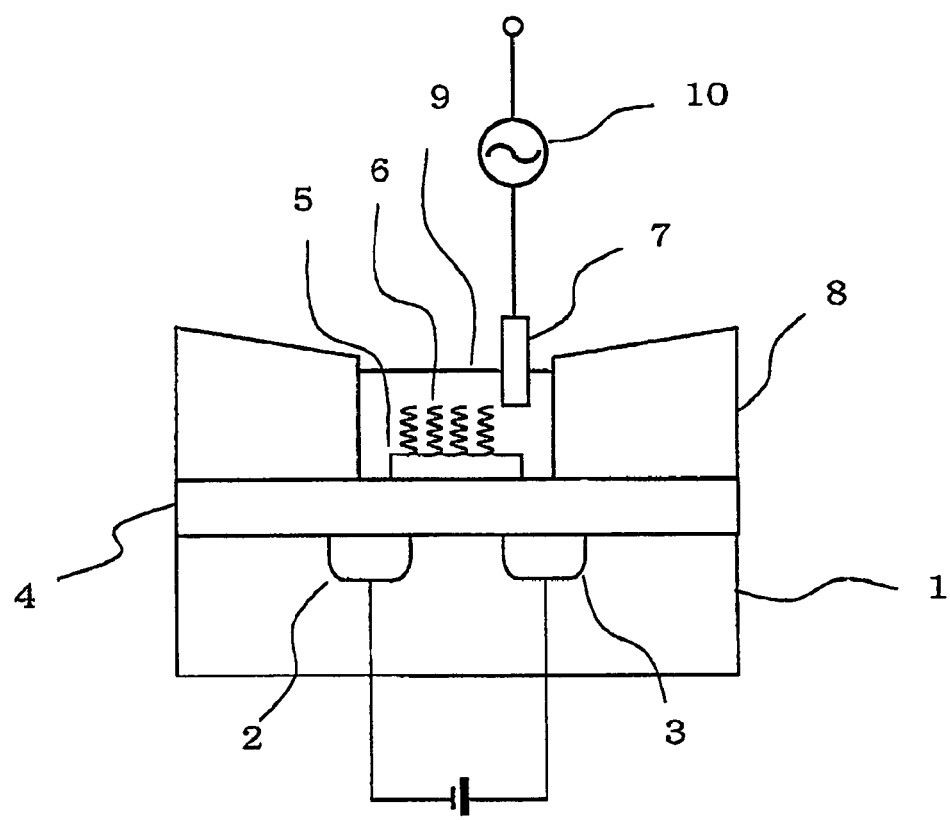
FIG. 1 is a diagram showing a structure of a biomolecular detection device of concern in this invention.

FIG. 1 is a configuration example of a biomolecular detection device of this invention. An insulated gate field effect transistor 1 used in this invention comprises a source 2 on the surface of a silicon substrate, a drain 3, and a gate insulator 4, and a conductive electrode 5 is installed on the gate insulator surface between the source and the drain. On the surface of the conductive electrode 5, a biomolecular detection probe 6 is immobilized. In an actual case of analysis, a conductive electrode 5 and a biomolecular detection probe 6 immobilized on its surface, and a reference electrode 7 are arranged in a sample solution 9 in an analytical cell 8, and an alternating current is applied by a power source 10 to the reference electrode 7. The presence of a subject of measurement such as DNA and proteins included in the sample solution 9 can be detected by detecting the changes in the electrical characteristics of the insulated gate field effect transistor 1, that are changes in the current value flowing between the source 2 and the drain 3, occurring before and after binding of a subject of measurement such as DNA and proteins in the sample solution 9 with a biomolecular detection probe 6.

As a biomolecular detection probe 6, nucleic acids such as a single-stranded DNA fragment, proteins and peptides such as antibodies, antigens and enzymes, and sugars can be used. The selection of a biomolecular detection probe is based on the differences in the specific binding force (affinity) that originates from the structure specific to the biological components. The reference electrode 7 gives a standard potential when stably measuring the potential changes based on the equilibrium reactions or chemical reactions occurring on the surface of the conductive electrode 5 in the sample solution 9. Generally, a silver/silver chloride electrode using saturated potassium chloride as an internal solution, or a mercury chloride (Calomel) electrode is used as a reference electrode. However, if the composition of the sample solution to be measured is constant, there is no problem if only a silver/ silver chloride is used as a pseudo electrode. An action point of the electrical characteristics of the insulated gate field effect transistor 1 (that is, a threshold value) can be adjusted by applying a specific voltage to the reference electrode 7.

Preferably the insulated gate field effect transistor 1 is a metal oxide semiconductor (metal-insulator semiconductor) field effect transistor (FET) using a silicon oxide as an insulating film. There is no problem with using a thin film transistor (TFT). Here a case of a biomolecular detection probe immobilized on the conductive electrode was described above; however, an ion sensitive film can be used instead of a biomolecular detection probe. For example, in the case of pH measurement, solid films such as silicon nitride ($Si_3N_4$) and tantalum oxide ($Ta_2O_5$) can be used as an ion sensitive film. In the case of potassium ion, a liquid film containing valinomycin can be formed.

Figure 19:
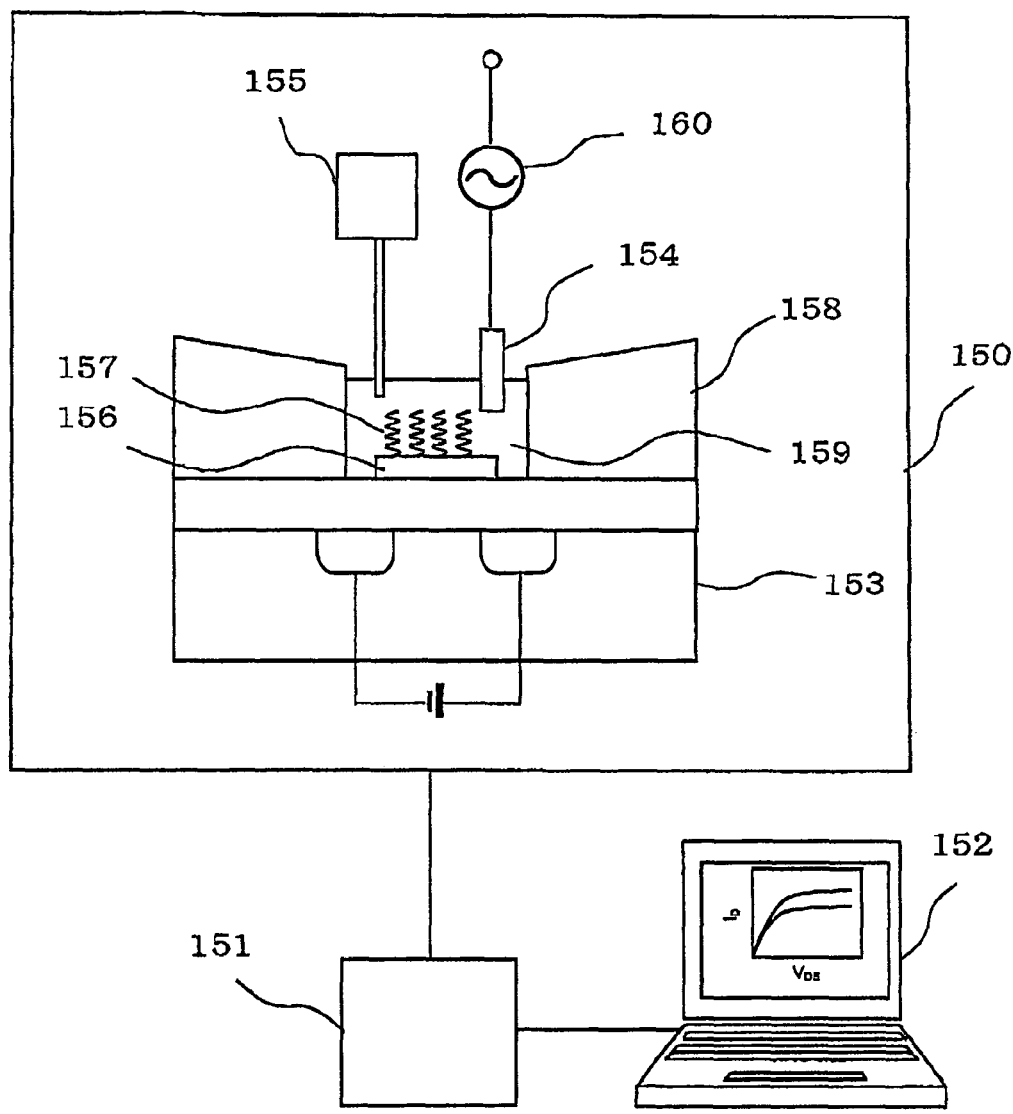
FIG. 19 is a block diagram showing a method for measuring biomolecules using a biomolecular detection device concerned in this invention.

FIG. 19 is a block diagram showing a method for measuring biomolecules using a biomolecular detection device of this invention. This measurement system comprises a measurement unit 150, a signal processing circuit 151, and a data processing system 152. In the measurement unit 150, an insulated gate type field effect transistor 153, a reference electrode 154, and a sample injection syringe 155 are arranged.

Measurement procedures are described below. Initially, a conductive electrode 156, a biomolecular detection probe 157 and a reference electrode 154 that are immobilized on the surface of the conductive electrode 156 are installed in a sample solution 159 located in the measurement cell 158, and an alternating voltage from a power source 160 is applied to the reference electrode 154. Subsequently, using a sample injection syringe 155, a sample is injected to the sample solution 159 in the measurement cell 158. When a biological material in the sample introduced binds to the biomolecular detection probe 157, the electrical characteristics of the insulated gate field effect transistor 153 change. The changes in the electrical characteristics are processed by the signal processing circuit 151; the data are processed in a data processing unit 152 to display the results.

Figure 2A:
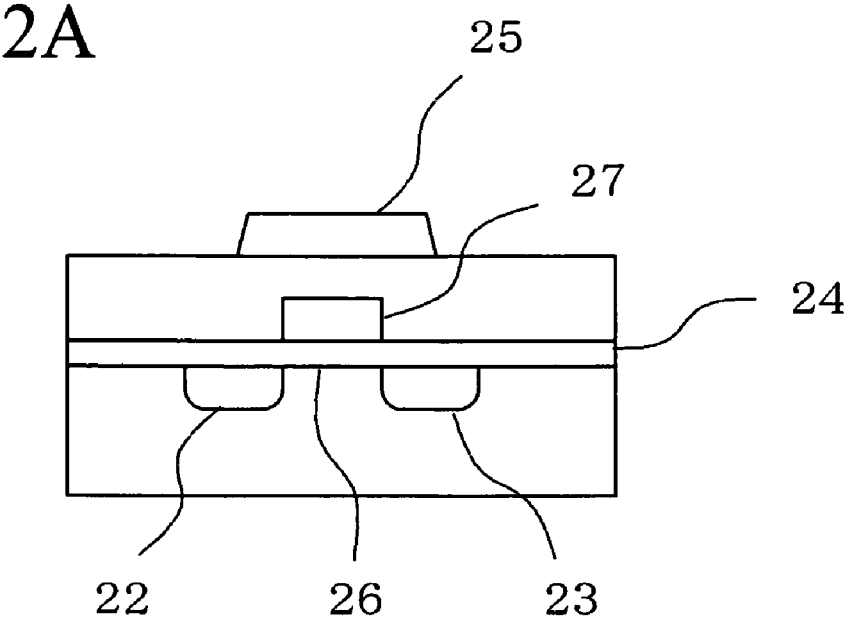
FIG. 2A is a plane view showing a structure of an insulated gate field effect transistor of concern in this invention.
Figure 2B:
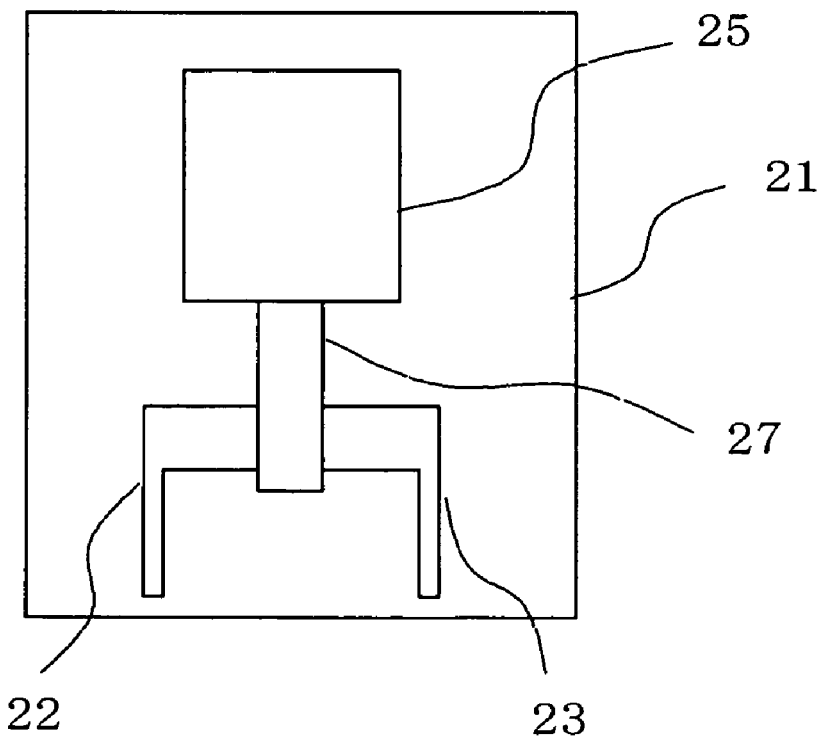
FIG. 2B is a cross-sectional view showing a structure of an insulated gate field effect transistor of concern in this invention.

FIG. 2 is a diagram showing an example structure of an insulated gate field effect transistor as another embodiment of this invention. FIGS. 2A and 3B respectively express a cross-sectional structure and a plane structure. In an insulated gate field effect transistor 21, a source 22, a drain 23, and a gate insulator 24 are formed on the surface of the silicon substrate, and a conductive electrode 25 is installed. The conductive electrode 25 on which a detection probe is immobilized and a gate 26 of the insulated gate field effect transistor are connected using a conductive wire 27. Using this structure, the conductive electrode 25 for immobilization of the probe can be formed at an arbitrary place in an arbitrary size. According to the subject of measurement, the electrode area for immobilization of the probe can be easily enlarged in order to improve measurement sensitivity. When preparing sensor chips for different subjects of measurement, an ordinary semiconductor process is applied to prepare a common area except for the probe immobilized electrode without preparing them individually, and lastly a subject of measurement are immobilized on the electrode. As a result, production costs can be reduced significantly.

Figure 3A:
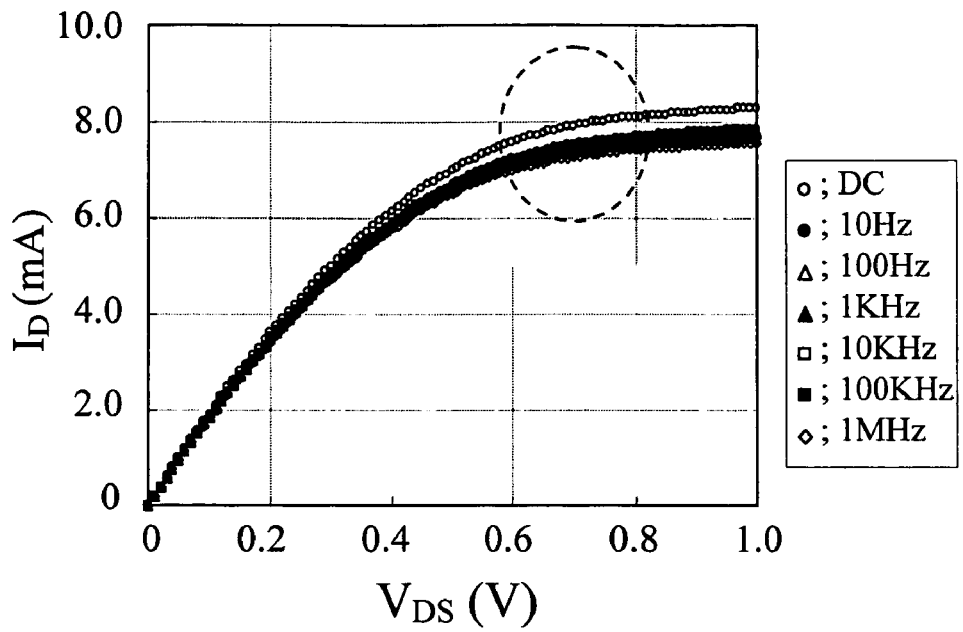
FIG. 3A shows an entire measurement range for the drain current values vs. frequency when an alternating current voltage is applied to the reference electrode.
Figure 3B:
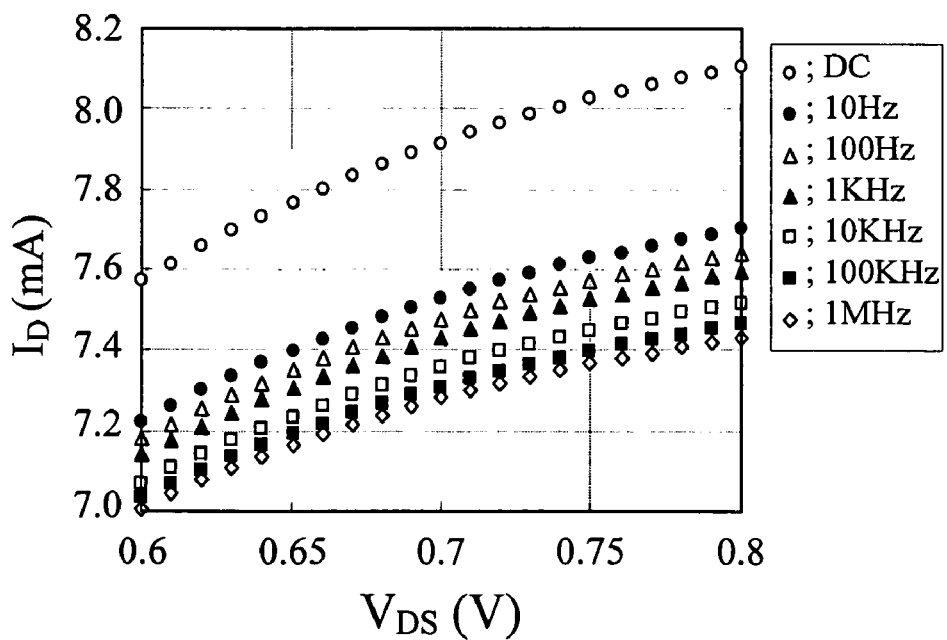
FIG. 3B is an enlarged view for the area enclosed in a dotted circle for the drain current values vs. frequency when an alternating current voltage is applied to the reference electrode.

FIGS. 3A and 3B are charts showing the effects when the effects of electric double layer on the conductive electrode 5 are eliminated by applying an alternating voltage to the reference electrode 7 as shown in FIG. 1. The current and voltage characteristics of the transistor, impedance, and electric capacity are measured using a semiconductor parameter analyzer (Agilent 4155C Semiconductor Parameter Analyzer) and impedance analyzer (Agilent 4294A Precision Impedance Analyzer). The contents in the solution were analyzed using a reference electrode (Ag/AgCl reference electrode) at the gate side. An alternating current voltage was applied to the gate at a center voltage: 50 mV, amplitude voltage: 50 mV. FIG. 3B is an enlarged view of the area enclosed by a dotted circle in FIG. 3A.

The conductive electrode 5 is used as a floating gate. An electric double layer is formed on the surface of the conductive electrode 5 in a solution and has an effect on the changes in the electrical characteristics of the insulated gate field effect transistor 1, causing a large background noise. In particular, if a noble metal such as gold and silver are used as a conductive electrode 5, this effect is significant. In the present embodiment, gold is used as a conductive electrode 5 and an alternating voltage is applied to the reference electrode 7 in order to eliminate the effect of this electric double layer. As shown in FIG. 3 (b), a drain current value ($I_D$) decreases when an alternating voltage is applied when compared to the application of direct current (DC), demonstrating an effect of eliminating the effects of electric double layer. In this case, as the frequency of the alternating voltage applied increases, a drain current value ($I_D$) monotonously decreases, showing a great effect of the application of alternating current voltage.

Figure 4A:
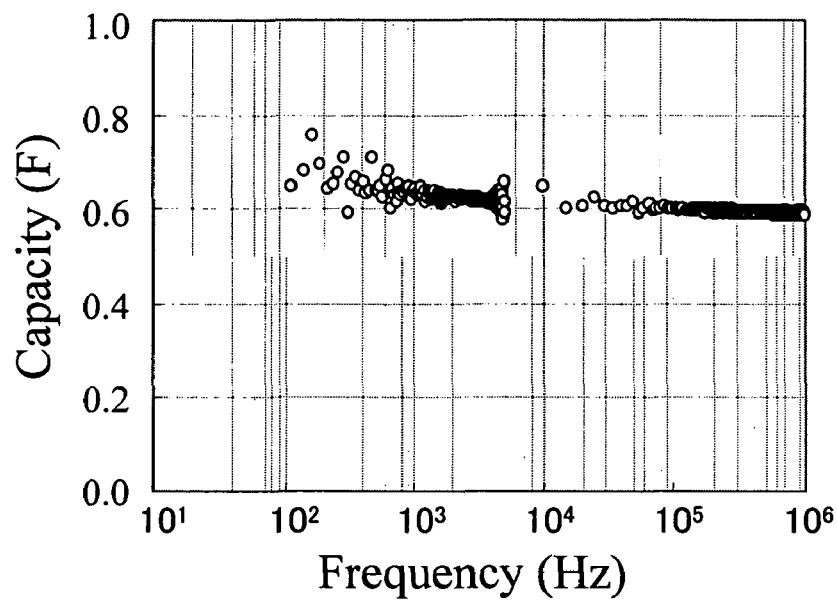
FIG. 4A shows data for a single substance (that is, in air), showing the measurement data indicating the relationships between the electric capacity of the insulated gate field effect transistor and the frequency.
Figure 4B:
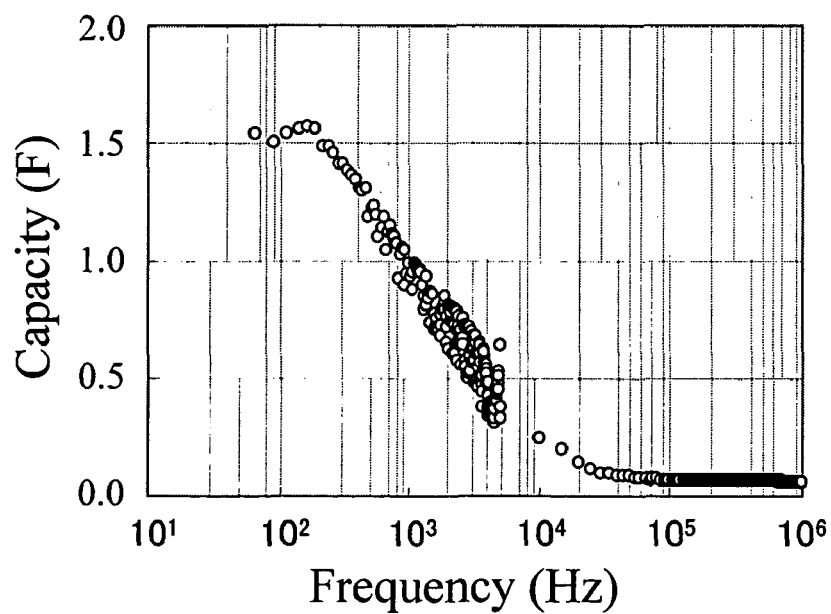
FIG. 4B shows data measured in a solution, showing the measurement data indicating the relationships between the electric capacity of the insulated gate field effect transistor and the frequency.

In addition, the size of the electric double layer on the conductive electrode is proportional to the size of the electric capacity. FIGS. 4A and 4B show the dependence of the electric capacity of the electric double layer on the gold electrode surface on the frequency of the voltage applied. FIG. 4A shows the electric capacity of the insulated gate field effect transistor, indicating almost a constant value that shows no dependence on the frequency. In contract, FIG. 4B shows the values in the solution, that is, the total of the electric capacity of an insulated gate field effect transistor alone and the electric capacity of the electric double layer on the gold electrode surface. In this case, a capacitance is assumed in the electrically equivalent circuit so that the reciprocal values of the measured values are the sum of the reciprocals of the respective values. As shown in FIG. 4B, the electric capacity approached the value of the electric capacity of the original insulated gate field effect transistor itself by applying an alternating current voltage, reaching almost the same value above 100 kHz. That is, if an alternating current voltage of 100 kHz or greater is applied, the effect of the electric double layer on the gold electrode surface can be almost completely eliminated.

Figure 5A:
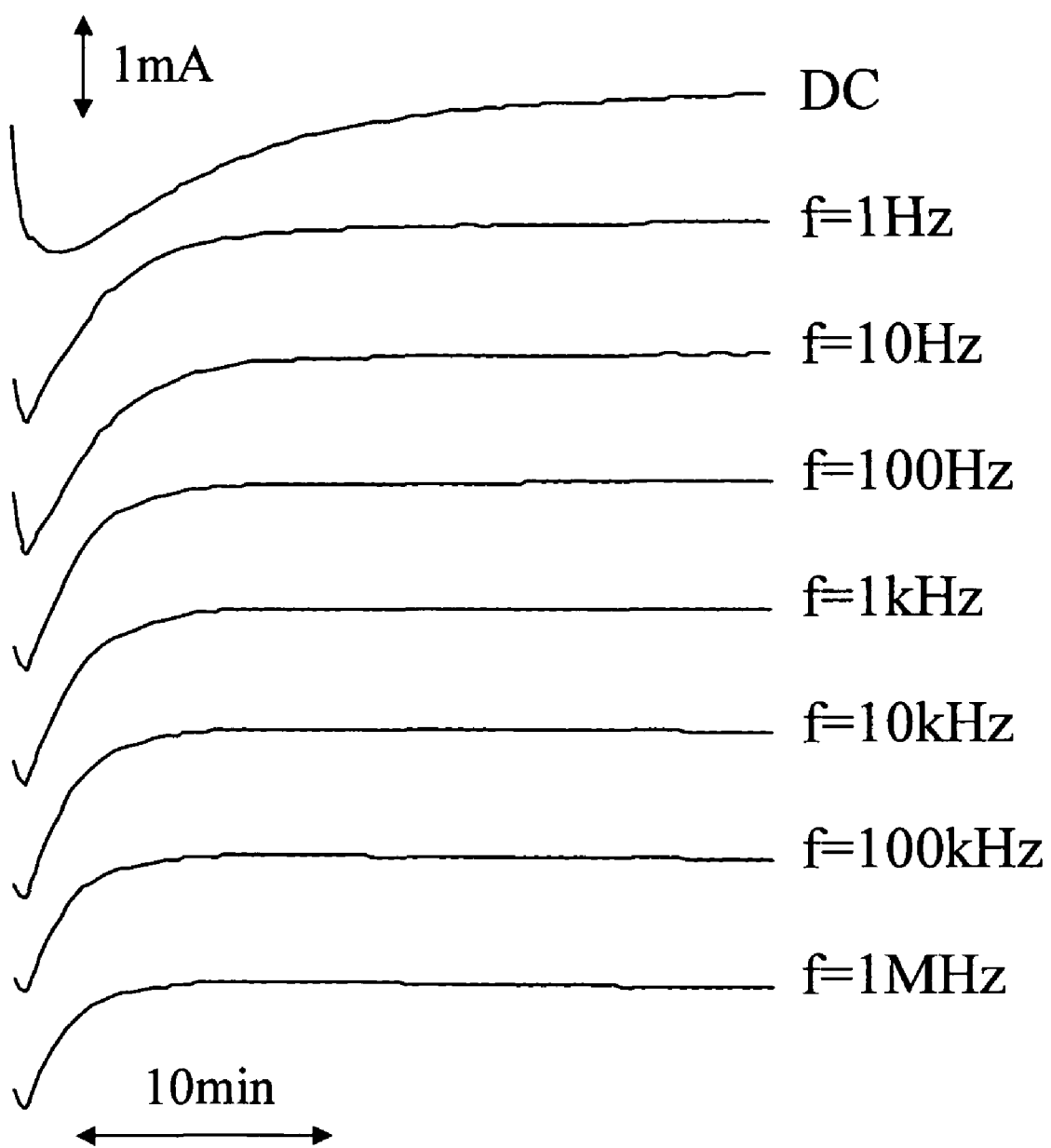
FIG. 5A is a chart showing the time-dependent changes from the beginning of measurement until the drain current is stabilized (in the case when a positive voltage is applied).
Figure 5B:
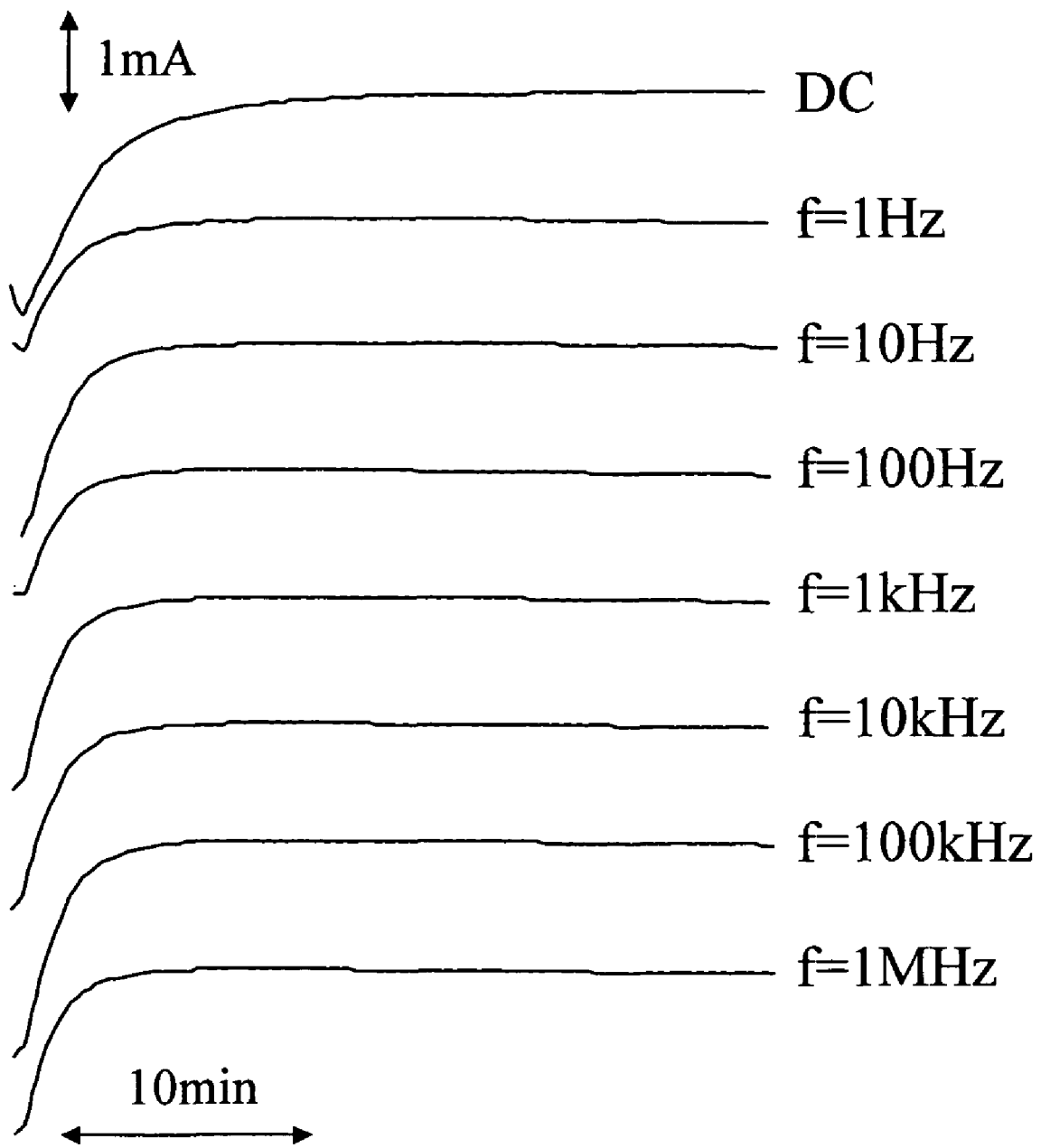
FIG. 5B is a chart showing the time-dependent changes from the beginning of measurement until the drain current is stabilized (in the case when a negative voltage is applied).

The effect of the application of alternating current voltage is described with reference to another embodiment. FIGS. 5A and 5B are charts showing the time-dependent changes until the drain current is stabilized from the beginning of the measurement. On the gold electrode surface of the insulated gate field effect transistor, a 21 base single stranded DNA (5'-HS-($CH_2$)$_6$-TACGC CACCA GCTCC AACTA C-3', a complementary sequence of k-ras coden 12 gene) was fixed by the bonds with thiol and gold via 6 carbon chains. FIGS. 5A and 5B represent the time-dependent changes in the drain current in the case when a positive voltage was applied (FIG. 5A) and a negative voltage was applied (FIG. 5B), respectively. In the normal measurement, direct current is used for the application of voltage to the reference electrode, but once a sample solution is introduced into the insulated gate field effect transistor, the voltage on the gold electrode surface changes and it takes about 30 minutes or longer until it is stabilized. However, as shown in FIGS. 5A and 5B, as the frequency of the voltage applied increases, in either case of application of a positive voltage or a negative voltage, the time until the drain current value is stabilized is found to be shortened.

Figure 6:
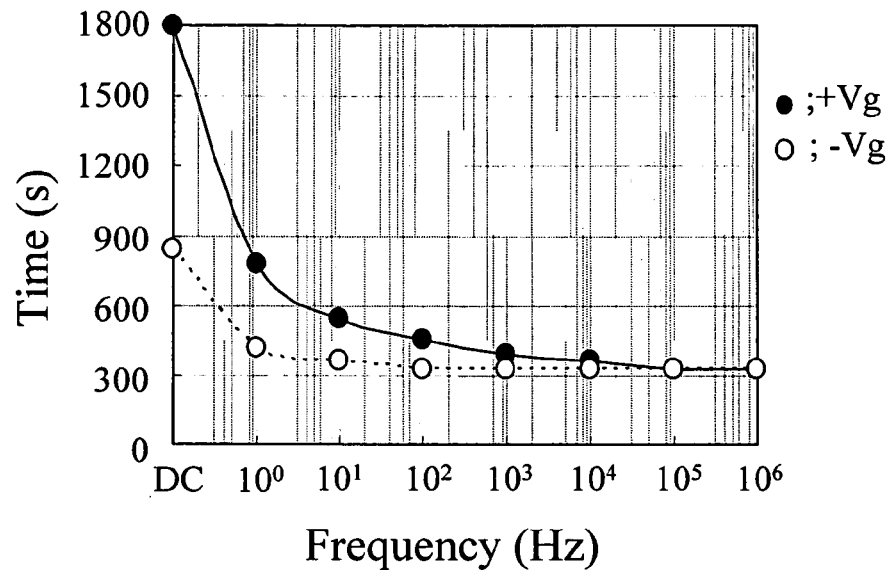
FIG. 6 is a chart showing the relationships between the time and the frequency from the beginning of measurement until the drain current is stabilized.
Figure 7:
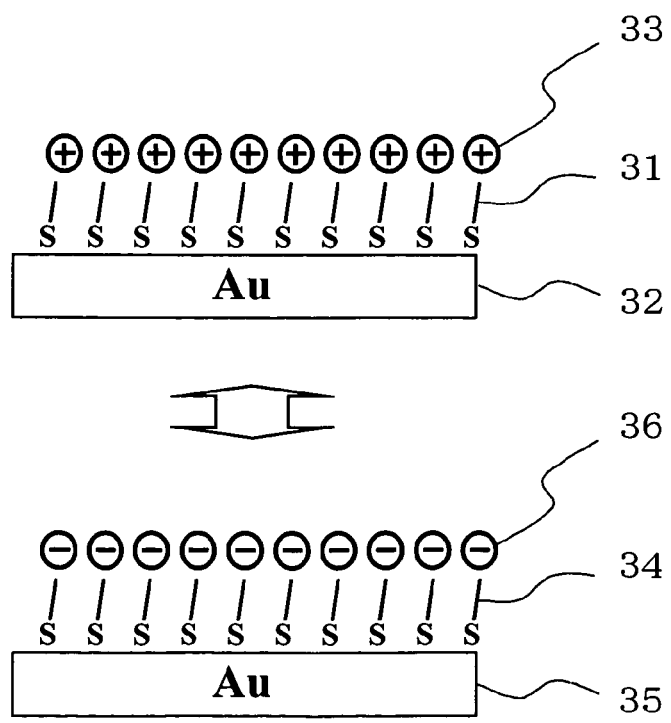
FIG. 7 is a diagram representing a charged status control method on the gold surface using alkane thiol.

The results are shown in FIG. 6 as the relationships between the frequency and the time to reach stabilization. As shown in FIG. 6, the time until stabilization became almost constant was reached when the frequency of the voltage applied was 1 kHz or greater either in the case of application of a positive voltage (indicated by ●) or in the case of application of a negative voltage (indicated by ○). In the case of a voltage with a low frequency, the time for stabilization was shortened in the case of application of a negative voltage compared to that in the case of a positive voltage. This seems to be due to the fact that DNA is negatively charged so that it is in a repulsive state against the gold electrode surface, that is, the DNA fragment is in a standing position.

The effect of the application of an alternating current voltage in this invention will be explained with reference to another embodiment. Generally, compounds having a thiol group are known to react with a gold surface to form Au—S bonds to form high density and high orientation self-assembled monolayers: SAMs. Using this property, the surface status can be easily changed by alkyl groups, terminal functional groups, and hydrophilic groups in the main chain. For example, if amino groups are used in the terminal functional groups of alkane thiol 31, the surface of the gold electrode 32 become positively charged 33, whereas if carboxyl groups are used in the terminal functional groups of alkane thiol 34, the surface of the gold electrode 35 becomes negatively charged 36. Using this property, a sample was prepared by changing the charges on the surface of the transistor gold electrode in this invention, in order to investigate the effect of the alternating current voltage applied. Samples used with different charged statuses on the gold electrode were as follows: alkane thiols having different terminal functional groups; amino groups (11-amino-1-undecantiol; 11-AUT), hydroxyl groups (11-hydroxy-1-undecantiol; 11-HUT), and carboxyl groups (10-carboxy-1-decantiol; 10-CDT). Immobilization on the gold electrode was carried out by immersion of a gold electrode in an alkane thiol ethanol solution for about 1 hour and followed by washing with ethanol and pure water before use.

In this experiment, as shown in FIGS. 5A and 5B, it took more than 1 hour until the drain current values are stabilized in the case of application of direct current voltage to the reference electrode. For this reason, in the case of application of direct current voltage to the reference electrode, the data were obtained after 1 hour of immersion in the sample solution. In the case of application of alternating current voltage at 1 MHz, the data were obtained after 5 minutes of immersion.

Figure 8A:
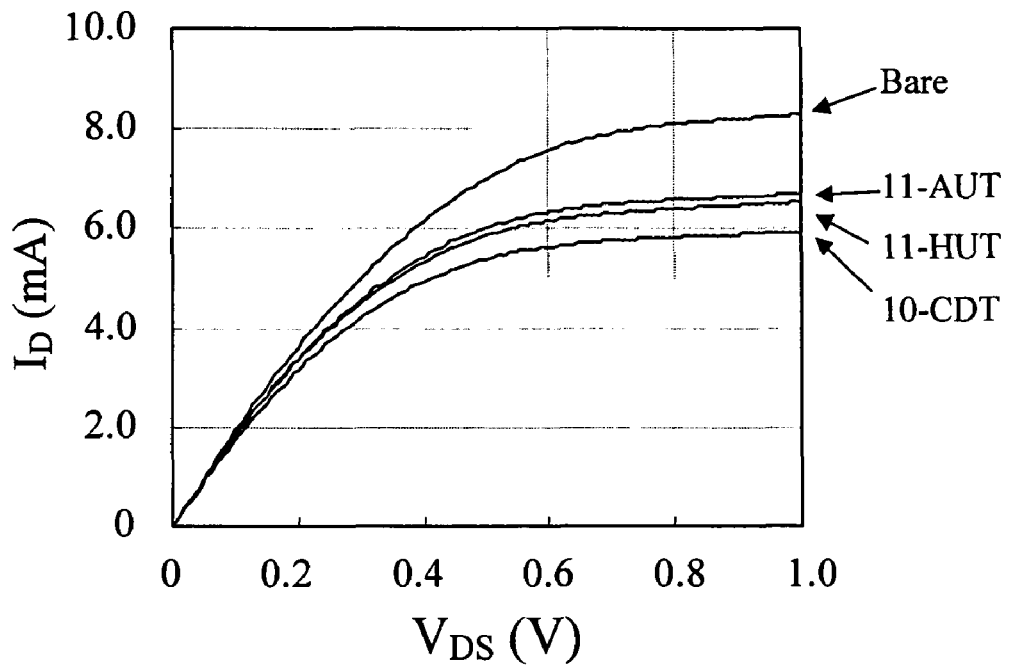
FIG. 8 is a chart showing an example of detecting the difference in the surface charges using a biomolecular detection device.
Figure 8B:
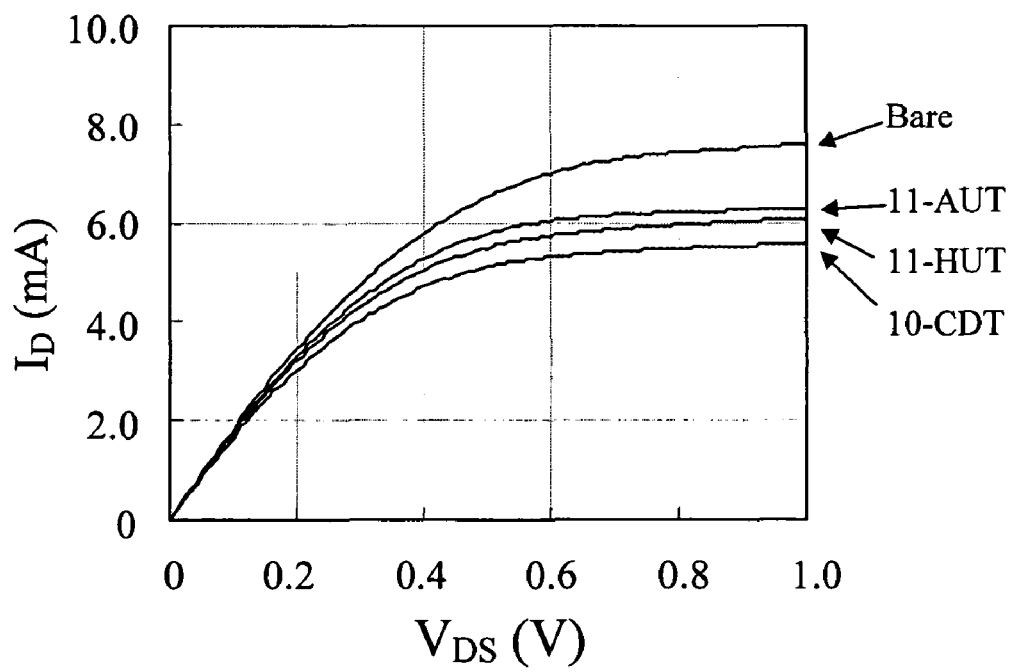

FIGS. 8A and 8B show the results when measuring the differences in the charged state. When alkane thiol was immobilized, the drain current declined when compared to the untreated gold electrode (indicated as bare in the figure). As a reflection of the differences in the terminal functional groups, the drain current flowed easier in the following order: amino groups (positive charges: +1), hydroxyl groups (neutral charges: ±0), carboxyl groups (negative charges: −1). That is, the drain current flows easier if positive charges are present on the gold electrode surface. In contrast, if negative charges are present on the gold electrode surface, it is difficult for the drain current to flow (FIG. 8A). This trend well represents the characteristics of the FET sensors, indicating normal operation of the sensors.

As shown in FIG. 8A, if an alternating current voltage (1 MHz) was applied to the gate (that is a reference electrode), the overall drain current became smaller and a difference in the drain current due to a difference in the terminal functional groups became larger, indicating the effect of application of the alternating current voltage. Using the area of the gold electrode used in this experiment (0.16 mm$^2$; 0.4×0.4 mm) and density of alkane thiol on the gold electrode (4 molecules/nm$^2$), we discovered that a difference in charges of approximately 1 pmol of molecules was detected in the present measurement. The density of alkane thiol on the gold electrode was measured by a voltammeter under strong alkaline conditions.

As another embodiment of this invention, a DNA detection method using a biomolecular detection device is described below.

Figure 9A:
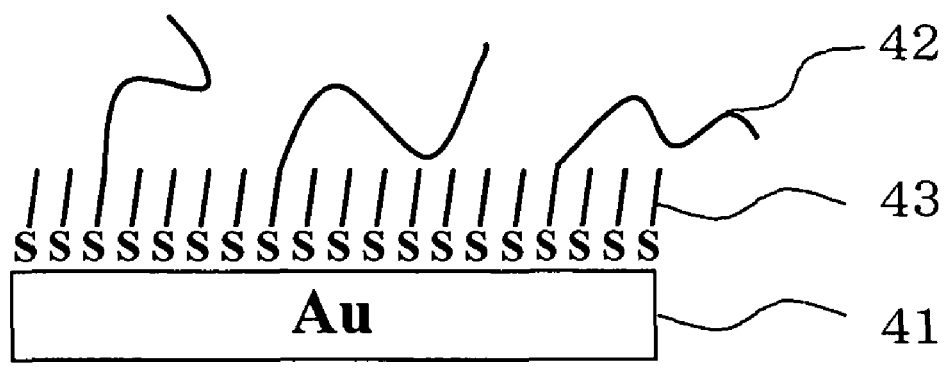
FIG. 9 is a diagram showing a method of DNA probe immobilization with high orientation on the metal electrode surface.
Figure 9B:
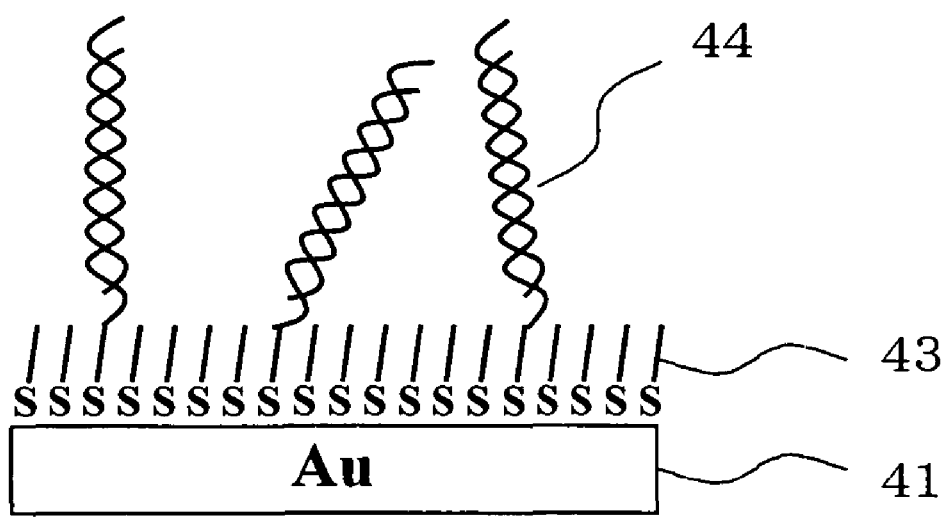

A biomolecular detection device used in this embodiment was an extended gate FET in which a conductive electrode and an insulated gate field effect transistor gate are connected with a conductive wire. In the present experiment, a gold thin film 41 was used as a conductive electrode. As shown in FIG. 9A, a DNA probe 42 was immobilized on the gold thin film surface 41 as below. After immobilization of the DNA probe 42, alkane thiol 43 was immobilized in order to control the orientation of the DNA probe 42 and to protect the surface of the gold thin film 41. When immobilizing DNA, if alkane thiol having amino groups is used, the DNA fragments are laid horizontally on the surface due to the interactions since DNA is negatively charged so that measurement stability declines (stabilization time and variations in the measurement values). Therefore, it is better to use alkane thiol having hydroxyl groups or carboxyl groups. For example, the alkane thiols to be used include mercaptoethanol, 6-hydroxy-1-hexanthiol, 8-hydroxy-1-octanethiol, 11-hydroxy-1-undecanthiol that have hydroxyl groups as a terminal group. Therefore, terminal groups can be selected from amino groups, carboxyl groups, or hydroxyl groups can be selected according to the charges in the subject of measurement. If physical adsorption on the electrode surface is the subject of concern, use of fluorocarbon causes fewer problems. If a sensor section in which a DNA probe 42 is immobilized on the surface of the gold thin film 41 is introduced to a sample solution, a double stranded DNA 44 is formed as shown in FIG. 9 (b).

Figure 10:
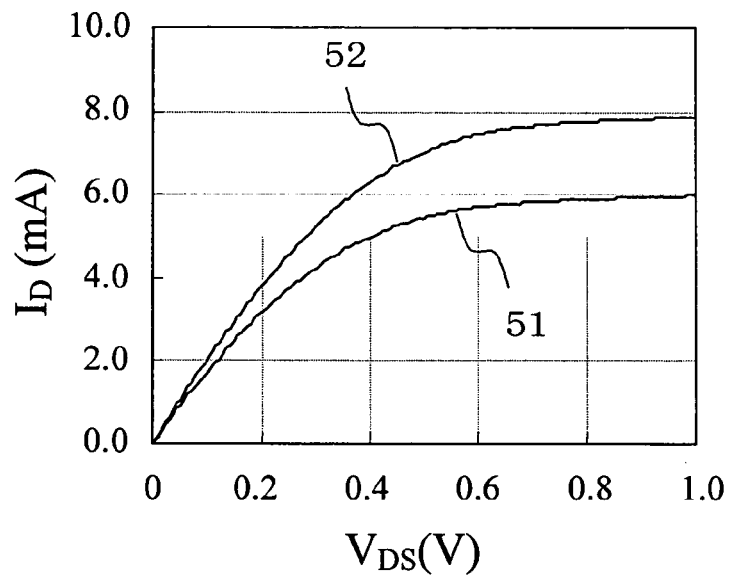
FIG. 10 is a chart showing an example of detection of a single stranded DNA and a double stranded DNA using an extended gate FET.

FIG. 10 shows the actual experimental results. The drain current 51 after the introduction of a sample (a double stranded DNA hybridized with a DNA probe) decreased when compared to the drain current 52 before the introduction of the sample (a single stranded DNA). This is due to the fact that the negative charges on the gold thin film surface have increased by forming double stranded DNA. The DNA probe was a 21 base single stranded DNA (5'-HS-(CH$_2$)$_6$-TACGC CACCA GCTCC AACTA C-3', a complimentary sequence of the k-ras coden 12 gene) and a sample DNA was a wild type (5'-GACTG AATAT TGTGG TAGTT GGAGC TGGTG GCGTA GGCAA GAGTG CCTTG ACGAT TAATT C-3'). This measurement was carried out by applying an alternating current voltage (frequency: 1 MHz, center voltage: 50 mV, amplitude voltage: 50 mV) to the reference electrode (Ag/AgCl reference electrode) at the gate side.

Another embodiment of this invention is described with reference to FIG. 11 which was a case when measuring the status of hybridization of DNA by changing the measurement temperature. This was based on the principle that the melting temperature (Tm) of a double stranded DNA to a single stranded DNA depends greatly upon the base sequence of DNA. That is, DNA having a different base sequence and a double stranded DNA having a single base substitution have different melting temperatures compared to a single stranded so that if a double stranded DNA is formed by hybridization of a sample with a immobilized probe and then the temperature around the DNA-immobilized electrode is altered, the drain current changes in response to the differences in the DNA having a different base sequence and in the DNA having a single base substitution. Therefore, a different base sequence and a single base substitution can be detected easily.

A DNA probe used in this experiment was a 21 base single stranded DNA (complimentary sequence to 5'-HS-(CH$_2$)$_6$-TACGC CACCA GCTCC AACTA C-3', k-ras coden 12 gene) and a DNA sample having two different bases. The DNA samples used were k-ras coden 12 gene wild type (5'-GACTG AATAT AAACT TGTGG TAGTT GGAGC TGGTG GCGTA GGCAA GAGTG CCTTG ACGAT AC$\overline{AGC}$ TAATT C-3') (the underlined section is a mutation site) and a mutant (5'-GACTG AATAT AAACT TGTGG TAGTT GGAGC TTGTG GCGTA GGCAA GAGTG CCTTG ACGAT AC$\overline{AGC}$ TAATT C-3') (underlined section is a mutation site). The theoretical difference in the melting temperature (Tm) was approximately 4° C. A DNA sample was hybridized around 20° C. and the drain current was measured while elevating the temperature. In this measurement, a direct current voltage of 0.5V was applied between the source and the drain and an alternating current voltage (frequency: 1 MHz, center voltage: 50 mV, amplitude voltage: 50 mV) was applied to the reference electrode at the gate side (Ag/AgCl reference electrode).

Figure 11:
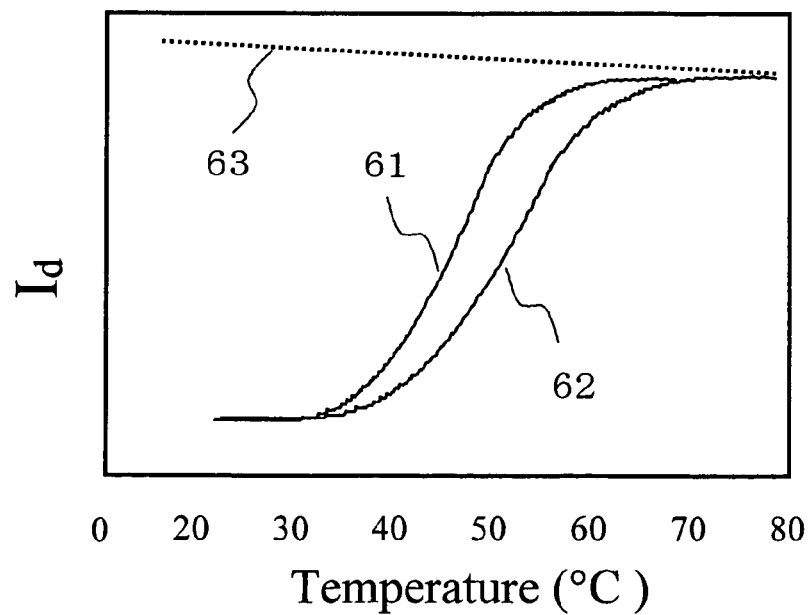
FIG. 11 is a chart showing an example of measuring the hybridization status under the temperature controlled conditions with the extended gate FET.

As shown in FIG. 11, the mutant type drain current 61 started rising at a lower temperature compared to the wild type drain current 62 due to the difference in the 2 base sequence in the DNA samples, distinguishing a difference between the two base sequences. As a reference, a drain current 63 of a single stranded DNA showing no complimentary base sequence was measured for temperature adjustment, but temperature adjustment can also be made using a temperature sensor. If the temperature adjustment is made using a temperature sensor, the corrections are made using the temperature dependency of the electrical characteristics of the FET sensor used. For example, the temperature variations detected by the temperature sensor are converted to the variations in the current values of FET and the differential portions are used for corrections.

Figure 12:
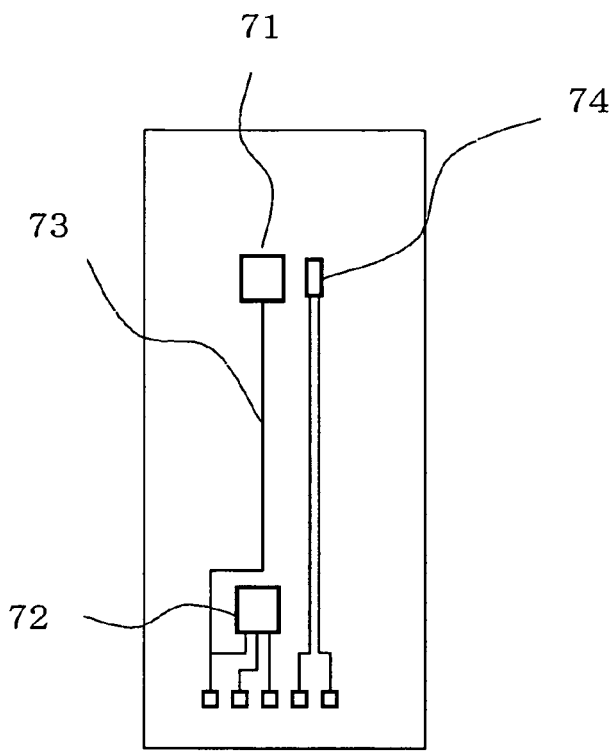
FIG. 12 is a diagram showing a structure of an insulated gate field effect transistor having a temperature sensor in another embodiment of this invention.

Another embodiment of this invention is explained with reference to FIG. 12 which is a structural example of the insulated gate field effect transistor loading a mixed temperature sensor. A biomolecular detection device prepared in this embodiment was a depletion type FET having an insulating layer of SiO$_2$ (thickness: 17.5 nm) which was an extended gate in which a conductive electrode 71 and the insulated gate field effect transistor gate 72 were connected with a conductive wire 73. A conductive electrode 71 for measurement and a diode 74 for measuring temperature are installed in this device.

A conductive electrode 71 was prepared using a gold electrode in a size of 400 µm×400 µm on the extended and enlarged gate. Measurements are generally made in an aqueous solution; this device must be operated in a solution. When measuring in a solution, it is important to operate in an electrode voltage range from −0.5 to 0.5V in which electrochemical reactions do not occur easily. For this reason, the preparation conditions for depletion type n-channel FET are adjusted, that is, ion implantation conditions for adjusting the threshold voltage (Vt) are adjusted so that a threshold voltage for FET is set at −0.5V. A diode for temperature measurement which was loaded on the device was an n$^+$/p joint type. The n$^+$/p joint diode temperature characteristics were represented by a temperature coefficient of approximately 1.8 mV/° C.

An extended gate FET used in this embodiment has the advantage that a sensing area can be set in an arbitrary size at an arbitrary location. In this device, a probe as a subject of measure can be immobilized at the final process when using chips prepared in the same process. Therefore, when preparing sensors for various subjects of measurement, the advantage is that the processes can be shared. Since a gold electrode for immobilization of the probe as used in this embodiment easily binds to a thiol compound to be stable, a immobilization process becomes easy by selecting a probe having a thiol group (generally an alkane thiol linker). In addition, a gold electrode is inactive and stable in a solution, which does not cause potential drift.

Figure 13:
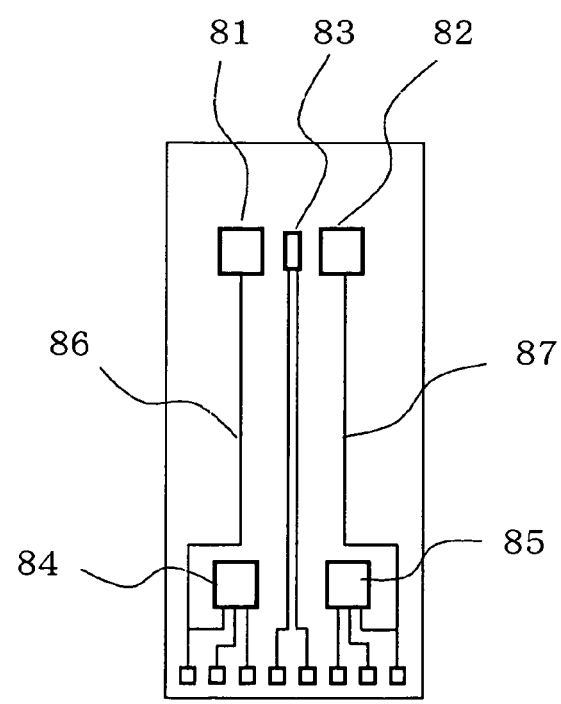
FIG. 13 is a diagram showing a structure of an insulating gate field effect transistor having a sample measurement electrode and a reference electrode in the same device in another embodiment of this invention.

FIG. 13 shows another embodiment of this invention wherein a sample measurement electrode and a reference electrode are loaded in the same device. This device comprises a sample measurement electrode 81, a reference electrode 82 and a diode for temperature measurement 83. The sample measurement electrode 81 and the reference electrode 82 in this device are connected to insulated gate field effect transistor gates 84 and 85, respectively using conductive wires 86 and 87. That is, this device has an extended gate type structure. An insulating layer is made of SiO$_2$ (thickness: 17.5 nm) and a gold electrode (400 µm×400 µm) as an electrode. Since this device is used in an aqueous solution, a threshold voltage of the FET is also set at near −0.5V. A diode for temperature measurement in this device was an n$^+$/p joint type.

Figure 14:
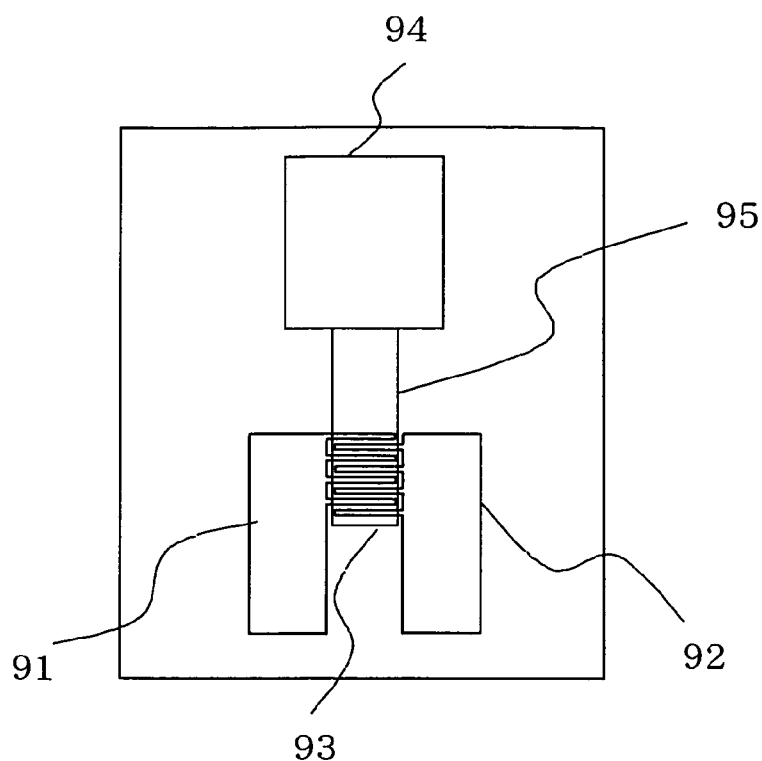
FIG. 14 is a diagram showing a structure of an insulated gate field effect transistor having a zigzag channel structure in another embodiment of this invention.

Another embodiment of this invention is explained with reference to FIG. 14. The principle of operation of the device used in this invention is based on the fact that the current between the source and the drain changes with the changes in the voltage on the gate surface when a subject of measurement binds to the probe immobilized on the surface of a gate or a floating gate (that is, a conductive electrode).

$$I_D = \frac{W \cdot \mu_c \cdot C_G}{L}\left[(V_G - V_t)V_{DS} - \frac{V_{DS}^2}{2}\right] \quad \text{[Equation 1]}$$

where W is a channel width, L is a channel length, µ$_c$ is mobility, C$_G$ is an electric capacity of binding between the gate insulator and the gold surface, V$_G$ is a threshold voltage forming a channel, V$_{DS}$ is a source/drain voltage.

In order to improve measurement sensitivity of this device, the changes in the current, that is W/L, can be set to be high. Traditionally, a channel width is extended and a channel length is shortened in order to improve measurement sensitivity so that the shape of the channel tends to have a structure longer in a longitudinal direction (for example, W/L=100/1). In this embodiment, as shown in FIG. 14, a source 91 and a drain 92 are arranged in a comb-like shape and zigzag shapes are made in-between to form a channel 93 in order to increase the ratio of the length of the channel to the width of the channel between the source 91 and the drain 92 (W/L=480/1). In this structure, a comb-like shape is formed in the 400 µm×400 µm shape so that a high sensitivity is achieved, which is approximately 6 times greater when compared to the conventional structure (for example, 400×5 µm) formed in the same-sized area. In this device, the conductive electrode 94 and the insulated gate field effect transistor gate (upper layer of the zigzag shaped channel 93) are connected using a conductive wire 95.

Figure 15:
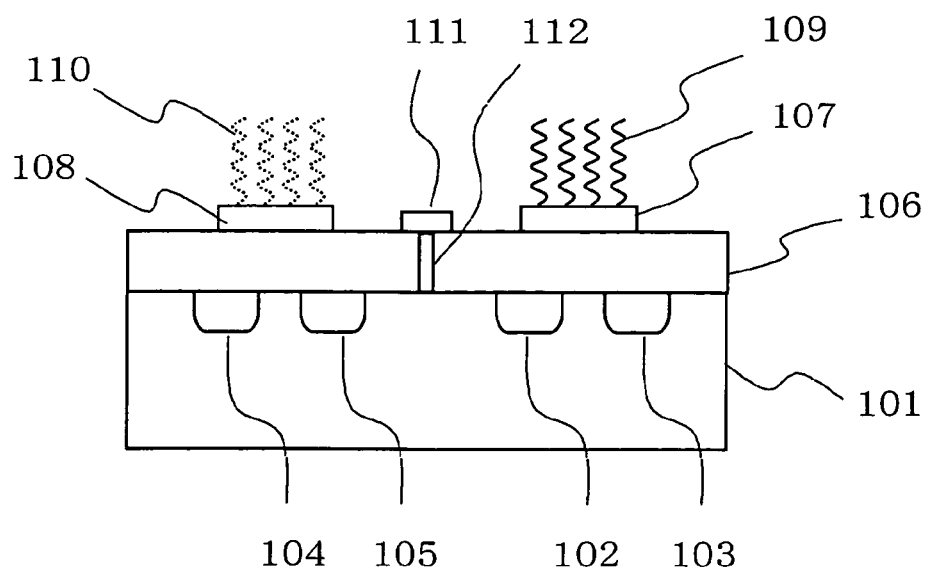
FIG. 15 is a diagram showing a measurement method using a differential system biomolecular detection device having a reference device in another embodiment of this invention.

Another embodiment of this invention is explained with reference to FIG. 15 which is a differential type biomolecular detection device having a reference device.

The device of this embodiment comprises a source 102 and a drain 103 of the measurement transistor, a source 104 and a drain 105 of the reference transistor, and a gate insulator 106 on the surface of a silicon substrate 101. Furthermore, conductive electrodes 107 and 108 are set on the gate insulator surface between the measurement transistor source 102 and the measurement transistor drain 103, and on the gate insulator surface between the reference transistor source 104 and the reference transistor drain 105, respectively. A biomolecular detection probe 109 and a pseudo molecular detection probe 110 are immobilized on the surface of the conductive electrodes 107 and 108, respectively. For example, in the case of measurement of DNA, the biomolecular detection probe 109 is a DNA probe having a complimentary base sequence to the target gene and the pseudo molecular detection probe 110 is a DNA probe having a different base sequence from the complimentary base sequence to the target gene. A pseudo reference electrode 111 is also installed on the same plane as the conductive electrodes 107 and 108. This pseudo reference electrode 111 is connected to the outside via a conductive wire 112. As a pseudo reference electrode, silver/silver chloride, gold, platinum, etc. can be used.

Figure 16:
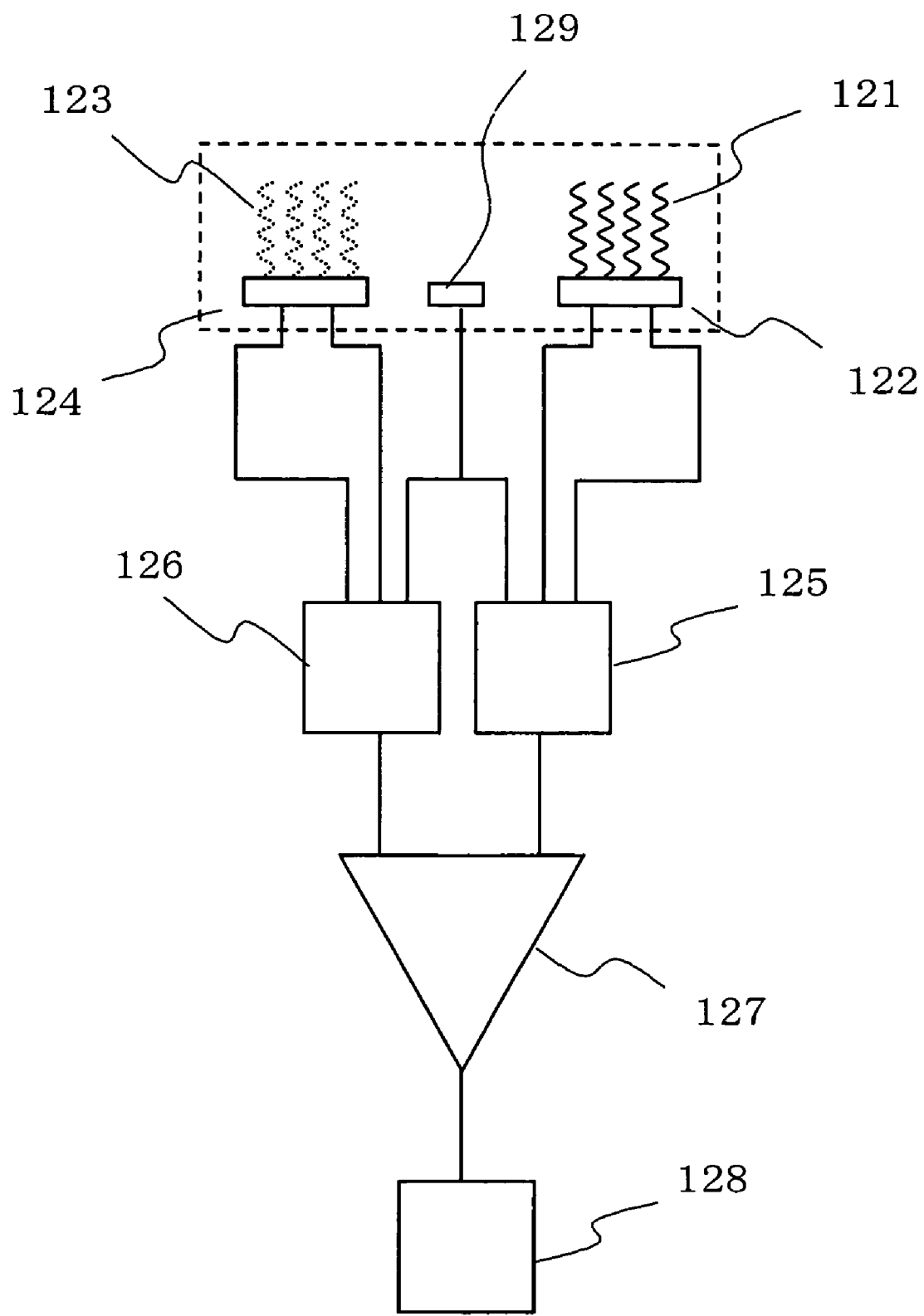
FIG. 16 is a diagram showing a measurement method using a differential system biomolecular detection device having a reference device in another embodiment of this invention.

In the actual measurement, as shown in FIG. 16, an output of the measurement transistor 122 on which a DNA probe 121 having a complimentary base sequence to the target gene and an output of the reference transistor 124 on which a DNA probe 123 having a complimentary base sequence to the target gene are entered to transistor driving circuits 125 and 126, respectively to measure the respective surface potential, and then entered to a signal processing circuit 128 via a differential amplification circuit 127. In order to measure the measurement transistor 122 and the reference transistor 124 stably, a common reference electrode 129 is installed as a standard for the measurement of voltage. In this measurement, a direct current voltage of 0.5V was applied between the source and the drain, and an alternating current voltage (frequency: 1 MHz, center voltage: 50 mV, amplitude voltage: 50 mV) was applied to the reference electrode at the gate side (Ag/AgCl reference electrode).

As a reference electrode, a silver/silver chloride electrode was used, but gold or platinum can be used without any problems. The changes in the output values due to the effects of atmospheric temperature and light and the output variances due to non-specific adsorption of impurities other than the measurement target materials on the surface of conductive electrodes are offset and corrected so that only the measurement target materials can be measured accurately. With combination of differential measurement with a pseudo reference electrode, the changes in the solution composition can be corrected and a compact solid type detection device can be implemented.

Figure 17:
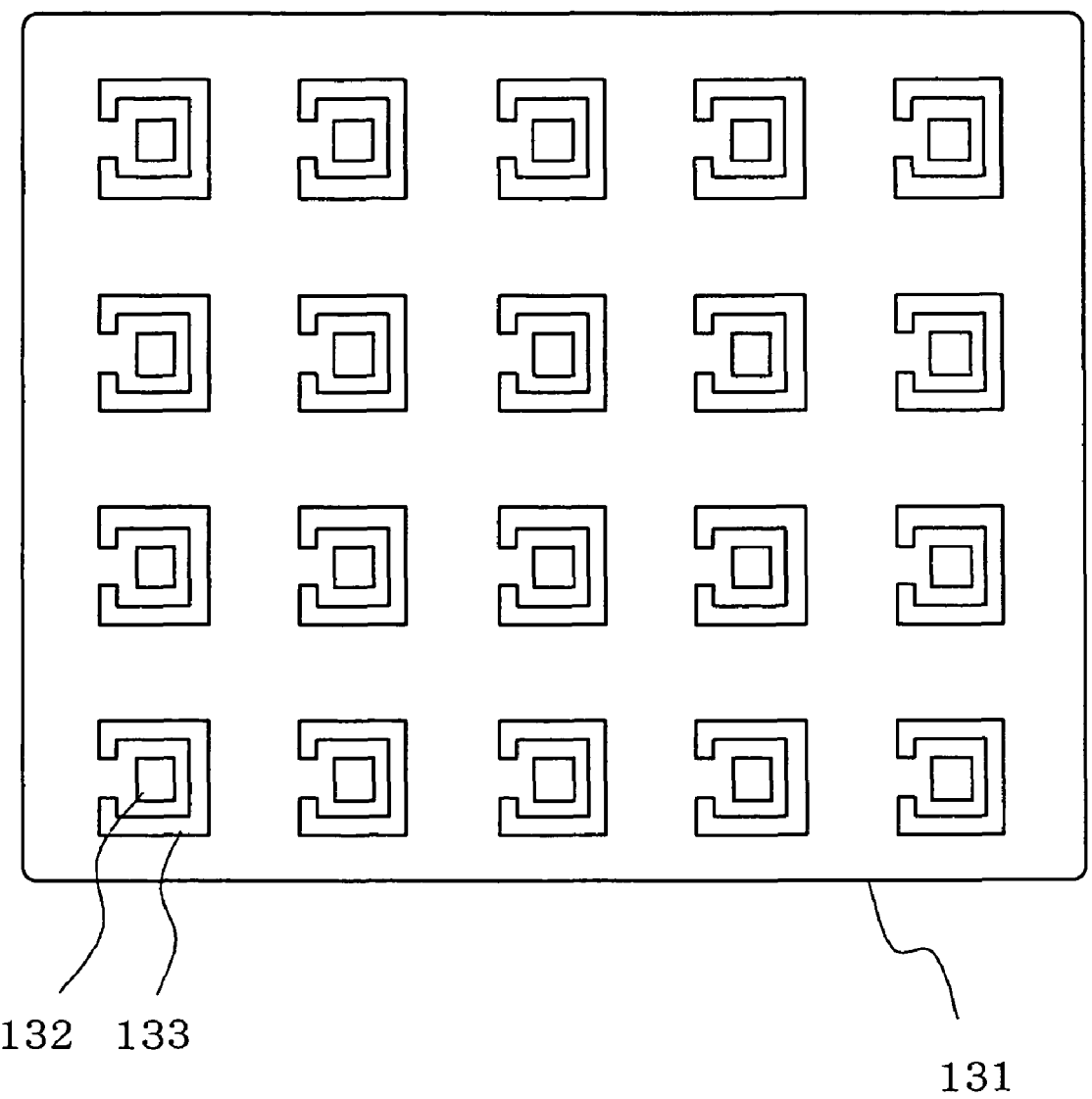
FIG. 17 is a diagram showing an example of an array device in another embodiment of this invention.

An example of an array device is explained with reference to FIG. 17 as another embodiment of this invention. In the array device of the embodiment, plural numbers of extended gate transistors are formed on a device substrate 131, and the surface conductive electrodes 132 are connected to respective gates of the extended gate transistors using a conductive wire. Pseudo reference electrodes 133 are formed as a 1 to 1 pair around the respective conductive electrodes 132. The effects among the adjacent electrodes including potential gradation can be reduced by forming a reference electrode as a pair to enclose each electrode 132. The advantage is that the electrical characteristics of transistors can be uniform by forming plural numbers of transistors on the same substrate. In this measurement, a direct current voltage of 0.5V was applied between the source and the drain, and an alternating current voltage (frequency: 1 MHz, center voltage: 50 mV, amplitude voltage: 50 mV) was applied to the reference electrode at the gate side (Ag/AgCl reference electrode).

Figure 18:
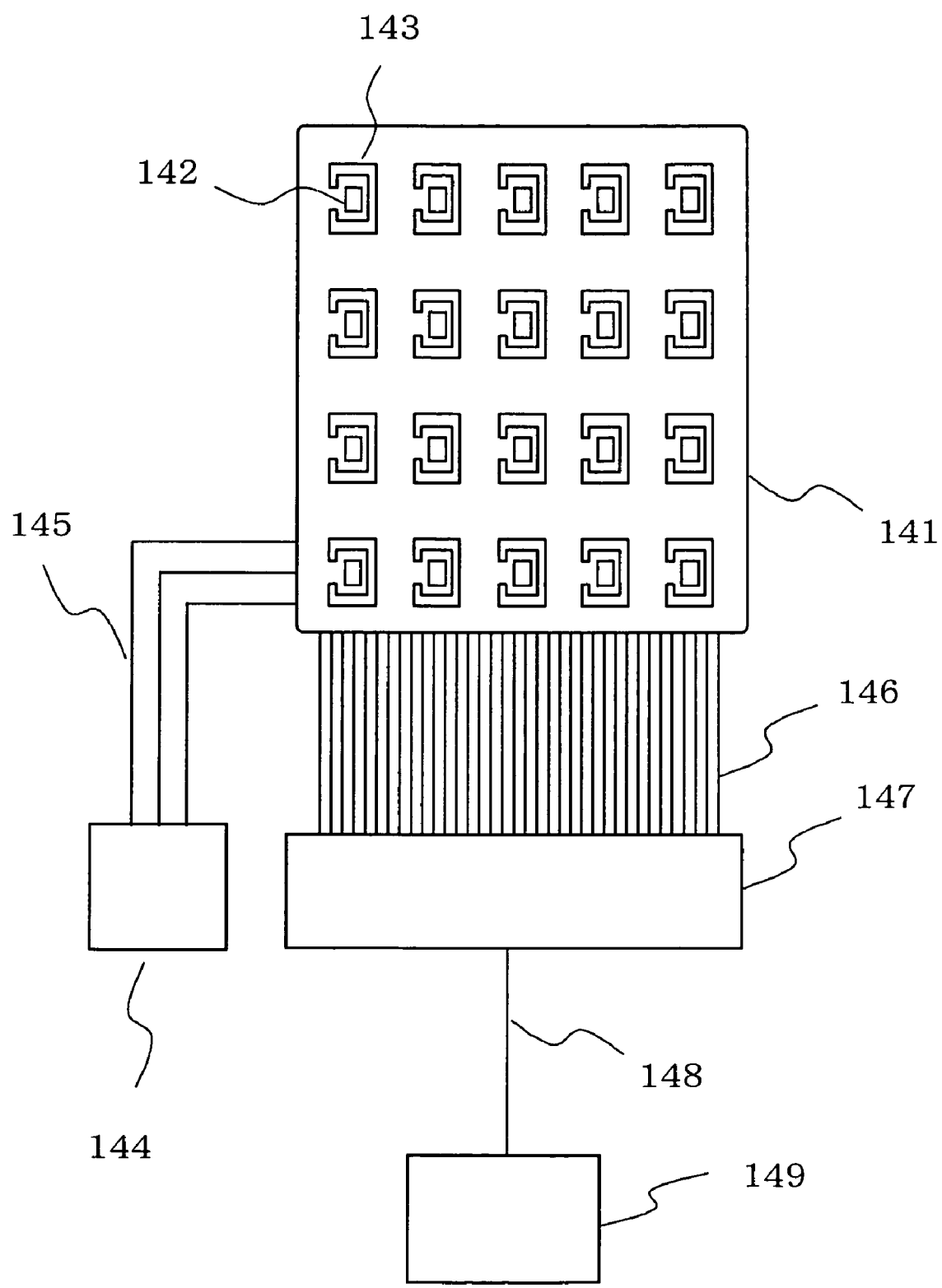
FIG. 18 is a diagram showing a measuring method using an array device in another embodiment of this invention.

When measurements are actually made using an array device, the same number of power sources to transistors and output lines of signals as the number of array elements must be provided. As shown in FIG. 18, when using an array device in which conductive electrodes 142 that are connected to respective extended gate transistor gates via conductive wire and pseudo reference electrodes 143 enclosing the conductive electrodes 142 are formed as a 1 to 1 pair on the array device substrate 141, an input line from the power source 144 to the respective transistors is shared, and the signal output lines 146 from the transistors are selected by a multiplexer 147 to be entered into a signal processing system 149 via a single signal output line 148 so that the number of output and input lines can be reduced. In addition, signal lines 146 and a multiplexer 147 are integrated on the array device substrate 141 to be able to reduce the number wirings. An array device is a metal insulator semiconductor field effect transistor (FET) using silicon oxide as an insulator, a thin film transistor (TFT) can also be used without any problems.

---

What is claimed is:

1. An analytical apparatus comprising:
a field effect transistor having a conductive electrode that is in contact with a sample solution, said conductive electrode having a probe immobilized on a surface thereof, said field effect transistor having a source, a drain and a gate, said conductive electrode being connected to the gate of said field effect transistor via a conductive wire;
a reference electrode that is in contact with said sample solution but not with said field effect transistor;
an AC power supply directly connected to the reference electrode for applying an alternating current voltage of a constant frequency with a direct current voltage superimposed thereon between said conductive electrode and the reference electrode; and
a DC power supply directly connected to the source of the field effect transistor for applying direct current between the source and the drain, and wherein changes in electrical characteristics of the field effect transistor are detected when the AC power supply supplies current to the reference electrode and the DC power supply supplies DC current to the source of the field effect transistor.

2. The analytical apparatus of claim 1, wherein said probe is nucleic acids, antibodies, antigens, and enzymes.

3. The analytical apparatus of claim 1, wherein the constant frequency of said alternating current voltage is 1 kHz or greater.

4. The analytical apparatus of claim 1, wherein said conductive electrode is made of gold.

5. The analytical apparatus of claim 4, wherein said probe is immobilized on the surface of said conductive electrode via an alkane thiol bonded at its one end.

6. The analytical apparatus of claim 1, wherein the shape of the channel electrically bonding between the source and the drain has a zigzag shape in said field effect transistor.

7. The analytical apparatus of claim 1, wherein said reference electrode is formed on the same substrate as said field effect transistor.

8. The analytical apparatus of claim 1, wherein a temperature-measuring device is installed on the same substrate as said field effect transistor.

9. An analytical apparatus, comprising:
a plurality of field effect transistors each of which is formed on a common substrate and has a probe immobilized on a surface thereof and a conductive electrode in contact with a sample solution, each said field effect transistor having a source, a drain and a gate, said conductive electrode is connected to the gate of a respective field effect transistor using a conductive wire;
a reference electrode that is in contact with said sample solution but not with said field effect transistors;
an AC power supply directly connected to the reference electrode for applying an alternating current voltage of a constant frequency with a direct current voltage superimposed thereon between said conductive electrode and the reference electrode; and
a DC power supply directly connected to the source of the field effect transistor for applying direct current between the source and the drain, and wherein changes in electrical characteristics of the field effect transistor are detected when the AC power supply supplies current to the reference electrode and the DC power supply supplies DC current to the source of the field effect transistor.

10. The analytical apparatus of claim 9, wherein the number of the reference electrodes is the same as said conductive electrodes, and each reference electrode is formed to substantially enclose the conductive electrode that is its pair electrode.

11. The analytical apparatus of claim 9, wherein said probe is nucleic acids, antibodies, antigens, and enzymes.

12. The analytical apparatus of claim 9, wherein the constant frequency of said alternating current voltage is 1 kHz or greater.

13. The analytical apparatus of claim 9, further comprising:
a field effect transistor having a conductive electrode on which a probe binding with a target is immobilized,
a field effect transistor as a reference having a conductive electrode on which a probe not binding with a target is immobilized, and
an active amplifier to which the output of the field effect transistor for said measurement and the output of the field effect transistor as a reference are input.

14. The analytical apparatus of claim 9, wherein a temperature-measuring device is installed on said common substrate.

15. An analytical method for detecting a measurement target substance comprising:
providing a sample solution, a reference electrode, and a field effect transistor having a conductive electrode, said conductive electrode having a probe immobilized on a surface thereof, said field effect transistor having a source, a drain and a gate, said conductive electrode being connected to a gate of said field effect transistor using a conductive wire;
bringing said conductive electrode and the reference electrode into contact with the sample solution but not with each other;

applying an alternating current voltage of a constant frequency with a direct current voltage superimposed thereon between said conductive electrode and the reference electrode that are in contact with said sample solution using an AC power supply connected directly to the reference electrode to apply the alternating current voltage of constant frequency with the direct current voltage superimposed thereon;

applying a direct current between the source and the drain; and measuring electrical characteristics of said transistor before and after the measurement target substance included in said conductive electrode forms a bond with said probe, wherein changes in electrical characteristics of the field effect transistor are detected.

16. The analytical method of claim 15, wherein the electrical characteristics of said transistor are measured while changing a temperature around said conductive electrode.

17. The analytical method of claim 15, wherein said probe is nucleic acids, antibodies, antigens, and enzymes.

18. The analytical method of claim 15, wherein the constant frequency of said alternating current voltage is 1 kHz or greater.

19. The analytical apparatus of claim 1, further comprising one of a voltmeter and an ammeter operatively connected between the source and the drain for measuring the electrical characteristics of the FET selected from the group consisting of a current or a voltage change across the gate.

20. The analytical apparatus of claim 9, further comprising one of a voltmeter and an ammeter operatively connected between the source and the drain for measuring the electrical characteristics of the FET selected from the group consisting of a current or a voltage change across the gate.

21. The analytical method of claim 15, further comprising one of a voltmeter and an ammeter operatively connected between the source and the drain for measuring the electrical characteristics of the FET selected from the group consisting of a current or a voltage change across the gate.

22. The analytical apparatus of claim 1, wherein the AC power supply applies the alternating current voltage and decreases a drain current of the field effect transistor generally in proportion to the constant frequency of the alternating current voltage.

23. The analytical apparatus of claim 1, wherein an amplitude of the direct current voltage is bigger than an amplitude of the alternating current voltage.

24. The analytical apparatus of claim 1, wherein an amplitude of the direct current voltage is 10 times of an amplitude of the alternating current voltage.

25. The analytical apparatus of claim 1, wherein the conductive electrode is connected to the gate of the field effect transistor on an end opposite that to which the probe is immobilized.

26. The analytical method of claim 15, wherein the conductive electrode is connected to the gate of the field effect transistor at an end opposite that to which the probe is immobilized.

27. The analytical apparatus of claim 1, wherein constant voltage is applied across the source and the drain.

28. The analytical apparatus of claim 1, wherein the changes in electrical characteristics comprise an electrical change across the source and the drain.

29. The analytical apparatus of claim 28, wherein the electrical change is selected from the group consisting of a change in voltage and a change in current across the gate.

30. The analytical apparatus of claim 1, wherein the electrical characteristics are impedance.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Synthetic DNA

<400> SEQUENCE: 1
tacgccacca gctccaacta c                                         21

<210> SEQ ID NO 2
<211> LENGTH: 71
<212> TYPE: DNA
<213> ORGANISM: Artificial Sequence
<220> FEATURE:
<223> OTHER INFORMATION: Synthetic DNA

<400> SEQUENCE: 2
gactgaatat aaacttgtgg tagttggagc tggtggcgta ggcaagagtg ccttgacgat    60
```

```
acagctaatt c                                                          71

<210> SEQ ID NO 3
<211> LENGTH: 71
<212> TYPE: DNA
<213> ORGANISM: Artificial Sequence
<220> FEATURE:
<223> OTHER INFORMATION: Synthetic DNA

<400> SEQUENCE: 3
gactgaatat aaacttgtgg tagttggagc ttgtggcgta ggcaagagtg ccttgacgat    60
acagctaatt c                                                          71
```